Figure 1:
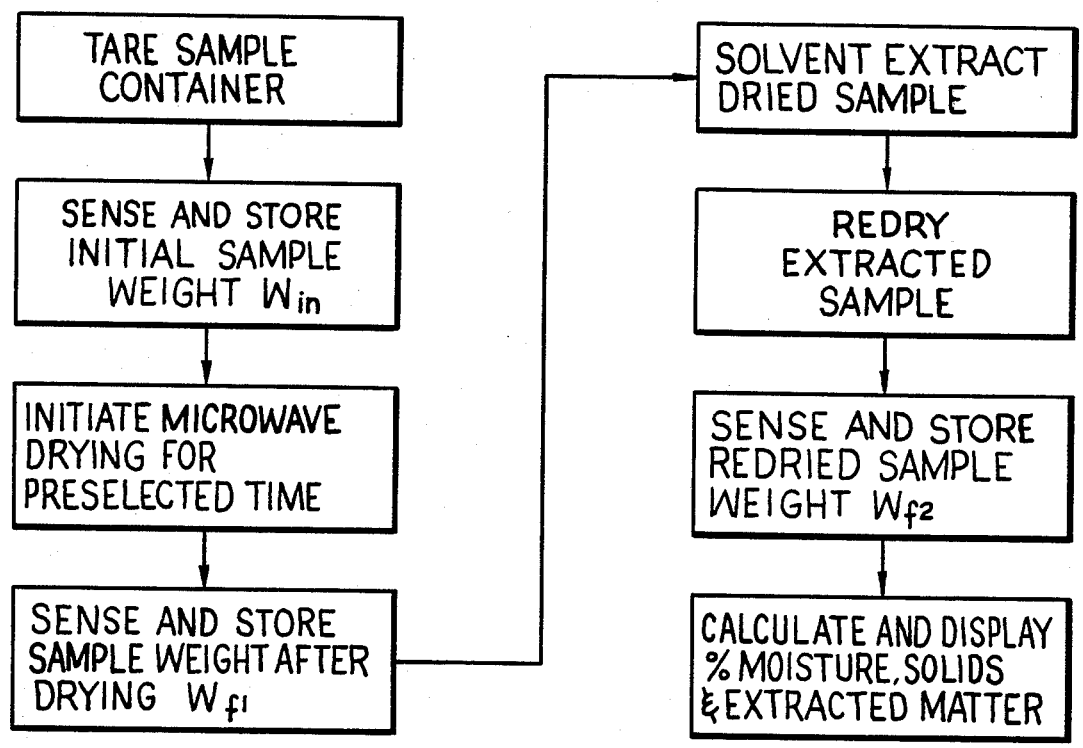

United States Patent [19]

Collins

[11] Patent Number: 4,554,132
[45] Date of Patent: Nov. 19, 1985

[54] ANALYTICAL APPARATUS FOR DETERMINING VOLATILES, SOLIDS, AND SOLVENT EXTRACTABLES IN A SAMPLE

[75] Inventor: Michael J. Collins, Matthews, N.C.

[73] Assignee: CEM Corporation, Indian Trail, N.C.

[21] Appl. No.: 445,199

[22] Filed: Nov. 29, 1982

Related U.S. Application Data

[63] Continuation of Ser. No. 21,986, Mar. 19, 1979, abandoned.

[51] Int. Cl.$^4$ .................. G01N 5/04; G01N 22/00; G01N 22/04; G01N 25/14
[52] U.S. Cl. .................................... 422/68; 73/76; 422/74; 422/78; 436/43; 436/178
[58] Field of Search .............. 73/53, 61 R, 76; 422/63, 68, 69, 74, 78; 436/178, 908, 43

[56] References Cited

U.S. PATENT DOCUMENTS

| | | | |
|---|---|---|---|
| 1,255,329 | 2/1918 | Mojonnier | 422/74 |
| 3,136,609 | 6/1964 | Ciagne | 422/74 |
| 3,673,852 | 7/1972 | Davis | 73/76 X |
| 3,752,651 | 8/1973 | Bush | 422/68 X |
| 3,813,918 | 6/1974 | Moe | 73/76 X |
| 3,890,825 | 6/1975 | Davis | 73/76 X |
| 3,909,598 | 9/1975 | Collins et al. | 73/76 X |
| 4,072,275 | 2/1978 | Bartels et al. | 209/453 X |
| 4,106,329 | 8/1978 | Tabahashi et al. | 73/76 X |
| 4,165,633 | 8/1979 | Raisanen | 73/76 |
| 4,168,623 | 9/1979 | Thomas | 73/76 |
| 4,203,727 | 5/1980 | Simpson | 423/578 A X |
| 4,246,184 | 1/1981 | Pressick et al. | 260/412.4 |

FOREIGN PATENT DOCUMENTS

1293127 10/1972 United Kingdom .................. 422/68

OTHER PUBLICATIONS

Chemistry and Testing of Dairy Products, Chapters 4 and 5, pp. 71–137, 1977.

*Primary Examiner*—David L. Lacey
*Assistant Examiner*—Robert J. Hill, Jr.
*Attorney, Agent, or Firm*—H. M. Adrian, Jr.

[57] ABSTRACT

An apparatus and method for quantitatively measuring volatiles, solids and solvent extractables is described which provides rapid and accurate determinations using microwave heating, electronic balance weighing and solvent extracting of solubles. The method involves subjecting a weighed sample to microwave drying for a preselected time, reweighing to obtain the dry weight and determine volatile loss, solvent extracting the dried sample to determine fats, oils and other extractables followed by final measurement of residual solids. The apparatus is preferably automated to sequentially actuate the required weighing, microwave heating, solvent extraction, redrying, reweighing and calculation of the percentages of volatiles, solvent solubles and solids.

The apparatus and method are particularly suited for analytical uses in the food and dairy industries.

9 Claims, 2 Drawing Figures

ANALYTICAL APPARATUS FOR DETERMINING VOLATILES, SOLIDS, AND SOLVENT EXTRACTABLES IN A SAMPLE This is a continuation of application Ser. No. 021,986, filed Mar. 19, 1979, now abandoned.

INTRODUCTION

This invention is directed to an analytical apparatus and method for determining solids, volatiles and solvent extractable substances contained in a substance and, more particularly, it is directed to a method and apparatus for quantitatively determining moisture, solids and fat content of food products, waste products, blood and other organic materials.

The invention more particularly is directed to rapid quantitative analysis of materials which may have a high water content, which thus require the evaporation of such water to determine the solids and other materials present without removing or destroying the other materials in the process of removing the water or moisture. In particular, the rapid analysis is effected by the utilization of microwave heating to drive off the moisture followed by solvent extraction, the determination of solid content and the proportion of water, solids, oils, fat, etc., detected.

BACKGROUND OF THE INVENTION

The determination of volatiles in a given substance is a very routine determination which is made countless times every day in numerous industries. Almost all agricultural products, feed grains, food products and manufactured products such as textiles, films, coatings, paints, etc., are sold on the basis of the solid contents, the fat or oil content, moisture content or combination thereof. Consequently, these analyses must be run literally thousands of times daily in hundred of industries to determine precisely the value of the product based on the composition thereof. Corrections for moisture gain or loss during the production of a manufactured product or the storage of agricultural products and the like will directly affect the value of the product. The industry has thus established standards which directly relate to the value of the product, with price adjustments being made for variations in content.

The monitoring of moisture, solid, oil, fat and the like content requires considerable time in quality control processing and tends to insure that a proper or desired balance is obtained in the end product. Previous quality control analyses were time consuming, often taking hours to perform single tests due to the care needed in removing moisture, measuring fat content and the like so as not to destroy or decompose the same during the separation process. Thus, long, time consuming vacuum oven drying was often utilized as well as various viscosity, colormetric and the like tests, based either on titrations or other analytical procedures.

In the food industry, such as the dairy industry, the analysis of milk, cream, cheese, eggs, ice cream and the like are citical both in meeting government regulations as well as in assuring the quality of the product. Elaborate testing procedures have been developed over the years such as those set forth in the book, *Chemistry and Testing of Dairy Products,* 4th Ed., 1977, by Henry V. Atherton and J. A. Newlander, published by the AVI Publishing Co., Inc., Westport, Conn.

The industry, however, has long needed more accurate and rapid analytical methods to control the quality of these products. In the same manner, meat processing also has critical parameters of moisture and fat content which must be monitored and controlled. Corn, wheat, tobacco, peanuts and other food products all are subject to quality measurements determined by moisture, fat and/or oil content which is readily determined by the present invention. Blood analysis to determine the proportions of triglycerides, cholesterol and solid content is an important test to which the improved analytical procedures of the present invention are readily adopted. Wast products, including effluent streams, often require close monitoring under Environmental Protection Agent Regulations to control the solids, oil, grease and the like in such effluent streams. The present invention is ideal for such determinations in a rapid and precise manner.

It is therefore an object of the present invention to provide an apparatus and process which rapidly and precisely determines the proportion of moisture or volatiles in a given substance in a fraction of the time previously required.

It is an object of the present invention to provide a method and apparatus for measuring the solvent extractable materials in the residue of the substance from which the moisture or volatiles have been removed.

It is a further object of the present invention to provide an apparatus which does not depend upon operator skill but rather automatically weighs and records weight measurements as needed to measure and calculate the volatiles removed and solubles extracted.

It is yet another object of the present invention to provide a method of volatilizing the moisture in a sample being analyzed without decomposing the residual substances.

It is still another object of the present invention to provide a method and an apparatus which will calculate the percentage of materials volatilized, the percentage or amount residue material and the percentage or amount of solvent extractable material without subjection to human or operator error while at the same time substantially reducing the testing time to minutes or seconds per analysis.

These and other objects will become apparent to those skilled in the art from the description of the invention which follows.

THE INVENTION

In accordance with the invention a method is provided for measuring and determining volatiles, solids and solvent extractable solubles in a sample containing the same comprising weighing a sample to obtain an initial weight ($W_{in}$), subjecting the same to microwave drying for a preselected time, reweighing said sample to determine the dry weight ($W_{f1}$), solvent extracting said dried sample, redrying and reweighing said dried, extracted sample to obtain a final weight ($W_{f2}$) and determining the volatile, solids and solvent extractables from said obtained weights.

To effect the method of the present invention, an apparatus is provided for quantitatively determining volatiles, solids and solvent extractables in a sample comprising automatic weighing means with sample holding means, microwave heating means, solvent extracting means and recording and calculating means, said microwave heating means being directed at said sample holding means, said recording means being electrically connected to said weighing means to sense and record weights, said solvent extracting means communicating with said sample holding means and means for sequentially activating said weighing, recording, microwave heating, solvent extracting and calculating means in a predetermined sequence to determine the proportion of said volatiles, solids and solvent extractables.

The sequential activation of the various means of the apparatus can be effected by mechanical means, timing means, microprocessor means, computer means, electrical means and combinations thereof. Of these, the microprocessor is the preferred means for controlling the function of the apparatus and calculating the end results.

DETAILS OF THE INVENTION

Figure 2:
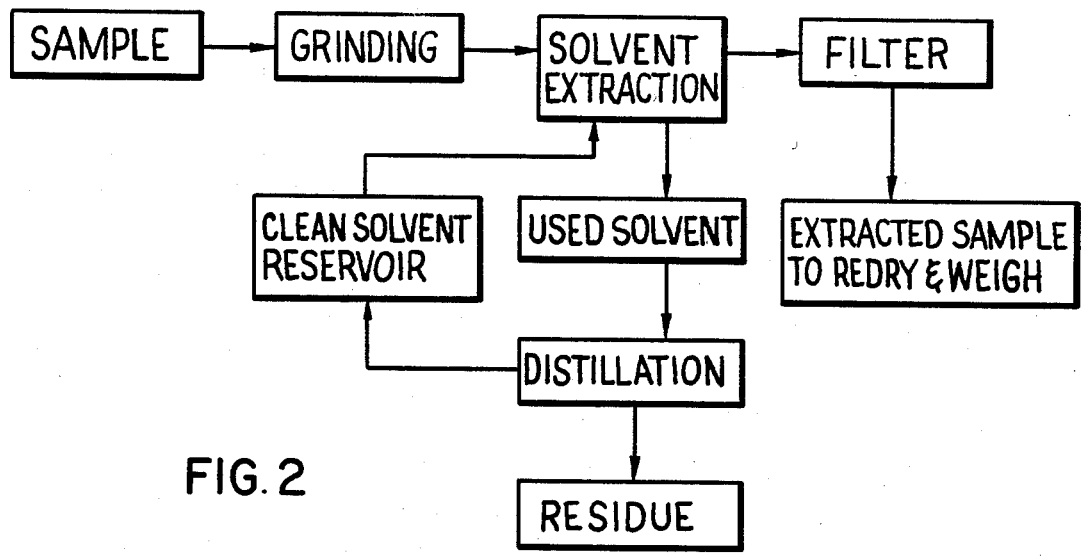

The invention will be more particularly described by reference to the drawings in which:

FIG. 1 is a schematic diagram illustrating the program sequence of the process of the present invention; and FIG. 2 is a schematic diagram of the preferred solvent extraction system illustrating the manner of recycling solvent for reuse.

The invention can be best understood by reference to the drawings in the more particularly described following description.

The apparatus and method of the present invention utilizes an automatic balance, preferably an electronic balance or other automatic balance means, which can be equipped to give an electrical signal proportional to measured weight. The automatic balance is positioned within a microwave heating chamber, such as a wave guide or oven, in the path of microwaves generated by a magnetron. Conveniently, conventional microwave ovens can be utilized modified as described herein. The preferred mode of positioning the weighing means in the microwave path is to utilize a top loading electrobalance which projects through the floor of the microwave oven. The sensing mechanisms of the balance are conveniently positioned beneath the floor of the oven sheltered from the microwaves. The parts of the balance projecting into the microwave path or oven are preferably composed of materials which are transparent to microwaves, thereby eliminating heating of the balance parts during the microwave heating phase. Typically, polypropylene, Teflon, polycarbonates, polyester and the like plastic materials are used for the stem and balance plate or sample holder. If desired, where additional heat is preferred to aid in drying the sample, heat generating parts such as a heat generating balance plate or sample holder or containers can be used. Glass is particularly suitable for this purpose because it normally has sufficient moisture trapped therein to generate heat when subjected to the microwave radiation.

The microwave oven may be of conventional design having proper radiation shielding. Alternatively, it can be of specific design to accommodate unusual size or shapes of samples, as well as to allow for the direct placement of the microwave radiation source in the oven or wave guide.

It is particularly desirable to make certain modifications of conventional microwave ovens to improve the heating efficiency for the present use and to prevent excessive reflection of the the microwaves back to the wave generator or magnetron, which could shorten the life thereof. Thus, it is desirable to utilize a radiation mixer to mix and disperse the radiation. Various radiation mixers are known in the art. Normally, they are rotating fan-like machines which reflect the radiation. Such mixers avoid the production of hot spots which could decompose or destroy part of the sample being tested.

Additionally, it is particularly desirable to equip the oven with other radiation absorbing materials or isolators. Radiation absorbing materials will couple with the radiation being admitted in the oven and thus prevent decomposition of the sample being processed due to excessive heat or radiation. Also, having a radiation-coupling material present, reflection back to the magnetron is reduced or eliminated. The coupling material further helps in preventing leakage of radiation from the oven.

A preferred coupling material is water, although any other polar substance could be used. It is preferred to circulate the coupling material through the oven in radiation transparant tubing or to utilize a reservoir from which the polar substance can be circulated and cooled. The amount of coupling material used can be thus readily regulated and adjusted to the desired volume and temperature.

Instead of using a coupling material, a radiation isolator can be used. An isolator is a terminal circulator which absorbs reflected radiation and prevents a buildup of heat. Such devices are also known in the art.

As is recognized in the art, microwave radiation is absorbed by water and polar organic molecules, causing an increase in molecular motion. Due to the absorption of radiation energy, the water and polar solvents are collectively heated and removed through vaporization and volatilization. It should be noted that when a polar material is present, other nonpolar volatiles could be removed from the sample being subjected to radiation due to the heating effect of the polar material.

Associated with the apparatus of the present invention is solvent extraction means, which are used to extract the solvent soluble material from the sample after the volatiles are removed by microwave heating. The solvent extraction system can be operated as an integral part of the apparatus or as an adjunct to the microwave heating and balance system.

In the solvent extraction step of the method and apparatus, a preselected solvent is applied to the sample after microwave drying to remove the moisture. The solvent is used in an amount sufficient to extract the solubles from the residual sample. This can be accomplished by several different methods. The different methods include both in situ extraction of the sample while in place on the balance or temporary removal of the sample from the balance during the extraction process. The method used will depend on the complexity of the apparatus used with the more simple apparatuses using a method wherein the sample is temporarily removed from the balance.

Because the method of the present invention does not require the recovery of the extractable for measurement but rather measures the weight loss, in situ extraction can be readily accomplished by placing the initial sample on or in filter paper. The initial drying thus leaves the sample deposited on the filter paper through which extracting amounts of solvent can be passed to extract the solubles. This can be readily accomplished while on the balance by provided for solvent feeding means and solvent draining means.

The more preferred method involves removal of the dried sample from the balance for extraction of the solubles. Again, the sample is initially dried on filter paper and the filter paper temporarily removed from the balance to effect the solvent extraction. When filter paper or pad is used in the process of this invention, it is preferable to use glass fiber filter paper because it not only aids in microwave heating by absorbing microwaves, but it does not have a water content which is volatilized and thus effects the measurements made therein. The removed dried sample material on the filter is placed in a solvent bath to thereby leach and extract the soluble substances. Preferably, the solvent bath is agitated or subjected to ultrasonic vibration to substantially reduce the extraction time.

The most preferred method of solvent extraction involves taring an extra filter pad with the initial sample being placed on the first filter pad out of contact with the extra filter pad. After the initial sample drying, the filter pad with the dried sample is removed from the balance, placed in the extracting solvent and ground by high speed shearing. This action rapidly extracts the solubles. The solvent and ground pad is then filtered through the extra filter pad to thereby recover the solids and first filter pad. A rinse of additional solvent can be used to insure recovery of all solids. The filter pad and collected solids are then returned to the balance.

FIG. 2, set forth in the preferred sequence of dried sample, is subjected to grinding, solvent extraction, and filter to recover the solids which are then redried and reweighed with the apparatus of the present invention. The used solvent is cycled through a distillation reboiler with the vapors being collected as clean solvent in a reservoir for subsequent reuse in another solvent extraction.

The solvents utilized herewith are selected for their propensity for extracting the particular extractable material which is known to be present in the dried sample. Depending on the particular type of samples which are expected to be analyzed, the solvents can be chosen accordingly or a more universal solvent utilized which is effective on a broad variety of samples. Typical solvents include ether, methylene chloride, carbontetrachloride, acetone, methanol, ethanol, various Freons, particularly trichlorotrifloroethane, combinations of Freon with acetone, ethanol and the like, as well as combinations of Freon and methylene chloride, particularly the azotropic compositions since they are more readily recovered through automatic distillation and recycling systems as set forth herein.

It is particularly desirable to utilize nonflammable solvents of which azotropic composition of Freon plus methylene chloride in a ratio of 50.5 Freon (trichlorotrifloretane) to 49.5 methylene chloride is particularly preferred. This combination is an excellent solvent for most fats and oils, is relatively low boiling for easy redistillation and recovery, has good stability and therefore is particularly suitable for the present invention.

The apparatus of the present invention can be controlled by a number of means as set forth above such as timers, electrical circuits, etc., but the preferred method of control is by means of a microprocessor, which is programmed to perform the functions of the apparatus in the desired sequence and to store the electrical signal from the electrobalance for subsequent calculation of the proportion of volatiles, extractables and solids. Further particularly desirable apparatus which can be modified as set forth herein to carry out the process of the present invention is that described in U.S. Pat. No. 3,909,598, which is incorporated herein by reference.

The process of the present invention commences by the operator placing a sample to be tested in the sample holder on the electronic balance, closing the microwave oven and initiating the start of the process by pushing a start button. The sample to be analyzed is preferably evenly distributed on some type of medium, such as a filter pad, to increase surface area exposure and to provide a convenient holding surface for the residual solids which will be produced during the process. Particularly suitable for this use are particulate glass substrates such as fiber glass filters, glass fiber filter pads or glass beads, because these materials have no moisture regain and provide good medium to distribute the sample with maximized surface area exposure.

The sample size can vary with the instrument size, electronic balance weight range and accuracy of the test results desired. The electronic balance and microwave oven is likewise sized for the intended usage. It should be noted that the basic usage of the present apparatus will be primarily for analytical purposes and, as such, analytical weight ranges and sizes are normally used. The apparatus is therefore best sized such that the sample will give at least about 100 milligram weight loss for the preferred electronic balance. This means that with a material containing 5 percent moisture, the minimum sample size would preferably be about 5 grams. With larger moisture losses and about 5 percent extractables, the weight size could also be about the same amount. The size of the sample should be adequate to give a weight change of the lesser ingredient well within the sensitivity of the balance. It is, of course, readily apparent that more sensitive electronic balances can be used for smaller samples, but such are generally impractical except for specialized usages. Therefore, the preferred sample weight will generally range between about 1 to 40 grams for most tests, depending on the amount of extractables and volatiles actually present. Weights up to about 1,000 grams or more can be used with proper sizing of the electronic balance With the sample in place, the process of the present invention proceeds according to FIG. 1, the sequence of which is programmed into the microprocessor. The initiation by the operator of the test causes the apparatus to sense and store the initial sample weight ($W_{in}$) followed by the initiation of the microwave drying. The drying time is preselected, based on such factors as the sample size, the magnetron capabilities, the unexpected volatile loss, time to achieve such loss, and other factors which can be readily determined by experimentation. Normally, for the average sample, microwave drying would be effected in about 20 seconds up to about 10 minutes, with longer times being required for higher percentages of volatiles or other factors such as those already noted. The particular drying time required is largely dependent upon the radiation absorption coefficient for the particular volatile material.

Having effected the microwave heating and drying for the preselected time, the weight of the sample is again sensed and stored by the microprocessor to provide a weight ($W_{f1}$).

The solvent extraction of the sample is then effected as previously described. The extracted sample is then redried by again subjecting it to a short period of microwave heating. The amount of heating required depends on the solvent utilized but normally such heating cycles can be relatively short due to the volatility of the solvents normally used. On completion of the redrying, the microprocessor again senses and stores the weight of the redried sample as $W_{f2}$. The proportions of the various components are thus readily calculated as follows by the following equations:

$$\text{percent volatiles} = \left(\frac{W_{in} - W_{f1}}{W_{in}}\right) 100$$

$$\text{percent solids} = \left(\frac{W_{f1}}{W_{in}}\right) 100$$

$$\text{percent extractables} = \left(\frac{W_{f1} - W_{f2}}{W_{in}}\right) 100$$

Such computations can be calculated, either by the microprocessor or by the operator, with the preferred method being by the microprocessor which then displays the calculation in readable form.

The readable form can be in any of various known forms such as printed copy, digital panel meter readings, direct electrical feed to other instruments, and the like. A preferred mode of readout is the digital panel meter. Such meters used in conjunction with the visible indicators are particularly helpful in normal testing procedures. Indicators designated by code, numerals, lights or the like signal the particular readout being shown on the digital panel meter. Such readouts can include initial sample weight, sample weight after initial drying, sample weight after solvent extraction, final sample weight, the difference between initial sample weight, and the percent weight loss or percent volatiles of the sample and percent extractables.

It is also convenient to provide operator controls having memory recall such that any one or more of the noted measurements can be recalled. Such recall is useful when the operator may want to recheck the initial weight and weight changes to check calculations. Push buttons or electrical switches can be provided so that the operator can re-examine these data on the digital panel meter. Where a printout reader is used, such recall is not necessary since the readout is on a printed copy.

The present apparatus is particularly advantageous for use in the dairy industry such as in the analysis of milk, cream, cheese, ice cream and the like because of its high speed and accuracy. Total determinations including moisture, solids and fat content generally require less than 5 minutes. The accuracy is precise because it involves a direct measurement, which is extremely accurate. In many cases, fat content is defined on the basis of solvent soluble material. Direct measurements eliminate the need for a calibration. The precision of the tests and apparatus is excellent because of the high resolution of electronic balances which are incorporated within the present apparatus.

While the present apparatus and method have been described more particularly as an analytical instrument, it is recognized that this apparatus and method can be readily adoped for other uses such as in-line production control, production usage and the preparation of dried samples for further testing and other end uses, as may be required in various commercial industrial processing. Consequently, the present invention is not intended to be limited except as noted in the appended claims.

What is claimed is:

1. An apparatus for quantitatively determining volatiles, solids and solvent extractables in a sample comprising in combination, automatic weighing means, sample holding means, microwave heating means, sample solvent extracting means, sample recovery means, recording and calculation means, said microwave heating means communicating with said sample holding means, said recording means being electrically connected to said weighing means to sense and record weights, said sample solvent extracting means communicating with said sample holding means and having means therewith to grind said sample holding means and means to recover the residue of ground sample holding means, and means for sequentially activating said weighing, recording, microwave heating, sample solvent extraction and calculating means in a predetermined sequence to determine the proportion of volatiles, solids and solvent extractables in a sample.

2. The apparatus of claim 1 wherein the sequential activating means comprises a microprocessor.

3. The apparatus of claim 1 wherein the sequential activating means comprises an analog computer.

4. The apparatus of claim 1 further comprising visual information readout means for displaying said determinations.

5. The apparatus of claim 1 wherein the sample holding means is glass fiber filter paper.

6. The apparatus of claim 1 wherein said sample holding means is a fiber sample filter pad and said sample solvent extracting means also includes sample filter pad container means and solvent supply means, said container means having said grinding means positioned therein and said solvent supply means communicating with said container means.

7. The apparatus of claim 6 wherein the grinding means is a high speed shearer.

8. The apparatus of claim 6 wherein the recovery means comprises a second filter pad.

9. The apparatus of claim 6 wherein said solvent supply means includes means for recycling solvent, said recycling means including solvent distillation and reboiler means, solvent reservoir means and solvent circulating means.

* * * * *